US008058629B2

(12) United States Patent
Long (10) Patent No.: US 8,058,629 B2
(45) Date of Patent: Nov. 15, 2011

(54) WRITING UTENSIL STERILIZATION APPARATUS

(76) Inventor: Catherine L. Long, Eagan, MN (US)

( * ) Notice: Subject to any disclaimer, the term of this patent is extended or adjusted under 35 U.S.C. 154(b) by 370 days.

(21) Appl. No.: 12/456,570

(22) Filed: Jun. 18, 2009

(65) Prior Publication Data

US 2009/0314956 A1    Dec. 24, 2009

Related U.S. Application Data

(60) Provisional application No. 61/132,486, filed on Jun. 19, 2008.

(51) Int. Cl.
*A61L 2/10*    (2006.01)

(52) U.S. Cl. .................. 250/455.11; 422/186.3

(58) Field of Classification Search .......... 250/455.11, 250/453.11; 422/22, 24, 186.3
See application file for complete search history.

(56) References Cited

U.S. PATENT DOCUMENTS

| 3,433,579 | A | 3/1969 | Runnion |
| 4,772,795 | A | 9/1988 | Sakurai et al. |
| 6,039,928 | A | 3/2000 | Roberts |
| 6,576,188 | B1 * | 6/2003 | Rose et al. ............ 422/20 |

* cited by examiner

*Primary Examiner* — Kiet Nguyen
(74) *Attorney, Agent, or Firm* — Kinney & Lange, P.A.

(57) ABSTRACT

A writing utensil sterilization apparatus includes a housing comprising an inlet for receiving a writing utensil and an outlet for dispensing the writing utensil, a UV light source disposed within the housing for emitting UV light, and a path disposed within the housing for guiding the writing utensil from the inlet to the outlet while exposing the writing utensil to the UV light.

20 Claims, 9 Drawing Sheets

WRITING UTENSIL STERILIZATION APPARATUS

CROSS-REFERENCE TO RELATED APPLICATION(S)

This application claims the benefit of U.S. Provisional Application No. 61/132,486 filed on Jun. 19, 2008, for "UV Pen Sterilizing Dispenser" by Catherine L. Long, which is incorporated by reference.

BACKGROUND

Public locations experiencing a large volume of human traffic can heighten the risk of individuals contracting disease via contact with common surfaces and items that numerous individuals have handled or touched. There is a recognized need for reducing the risk of transmitting disease from one person to another in such environments.

SUMMARY

A writing utensil sterilization apparatus includes a housing comprising an inlet for receiving a writing utensil and an outlet for dispensing the writing utensil, a UV light source disposed within the housing for emitting UV light, and a path disposed within the housing for guiding the writing utensil from the inlet to the outlet while exposing the writing utensil to the UV light.

DETAILED DESCRIPTION

An apparatus for sterilizing writing utensils comprises a housing having an inlet for receiving the utensil and an outlet for dispensing the utensil, and a UV light source disposed within the housing for sterilizing the utensil as it is guided by a path from the inlet to the outlet. Any infectious microorganisms that may have been transferred to the surface of the writing utensil through its handling or use are sterilized by the UV light, and the risk of transmitting disease to others who come into contact with the utensil is thereby greatly reduced or eliminated. The manner of operation is easily ascertainable just by viewing the apparatus without necessitating instructions be given each time it is used, thereby working well in public locations where numerous individuals may be required to use the apparatus for the first time. Further advantages of the apparatus are described in more detail below.

Writing utensils are by necessity handled and shared by numerous individuals at public places requiring the filling out of forms, such as hospital waiting rooms, hotel lobbies, and government polling places to name a few. If a diseased individual coughs or sneezes into his or her hands and then handles a writing utensil such as a pen or pencil, infectious microorganisms will be transferred to the surface of that utensil and come into contact with the next person who handles the utensil. Because writing utensils are frequently handled by one person right after another, even infectious microorganisms having a limited survival rate when exposed to air may have the opportunity to reach a subsequent individual using the writing utensil. Furthermore, most individuals have difficulty remaining consciously aware that commonly handled items such as writing utensils may harbor transmittable infectious diseases such as bacteria or viruses and may inadvertently touch their mouths after handling the utensil. The scenario of disease transmission via contact with writing utensils is further exacerbated by the fact that many people have habits including chewing the utensil or otherwise putting it in contact with their mouth, that heighten the risk of disease transmission above and beyond other commonly touched surfaces. The apparatus of the present disclosure addresses these problems in a unique and effective manner.

Figures 1A, 1B:
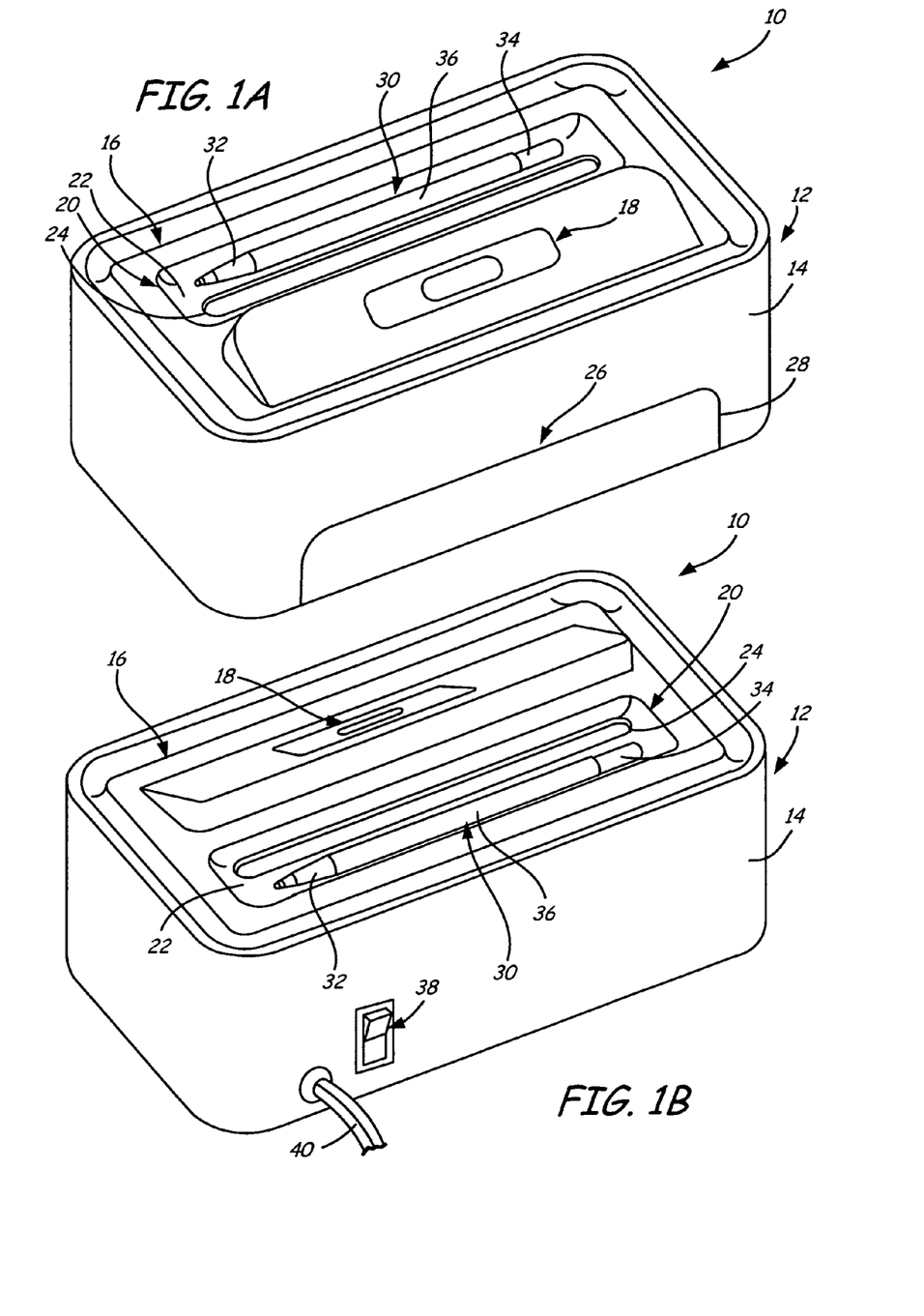
FIG. 1A is a perspective view of the front of a writing utensil sterilization apparatus with door closed.
FIG. 1B is a perspective view of the rear of the writing utensil sterilization apparatus shown in FIG. 1A.

FIG. 1A is a perspective view of the front of apparatus 10, showing housing 12 having housing exterior surface 14; lid 16 having user interface 18 and inlet 20 (having inlet surface 22 and inlet orifice 24); and outlet 26 having door 28, which is shown in a closed position. Further shown is writing utensil 30 comprising a first end 32, second end 34, and middle portion 36. FIG. 1B is a perspective view of the back of apparatus 10 shown in FIG. 1A, further showing on/off switch 38 and power cord 40.

Apparatus 10 is connected to an appropriate power source such as a wall outlet via power cord 40, and turned on with on/off switch 38. To operate apparatus 10 while in a powered on state for the sterilization of writing utensil 30, a contaminated writing utensil 30 is placed on inlet surface 22 or directly into inlet orifice 24. Inlet surface 22 preferably comprises a downward slope to inlet orifice 24 in order to facilitate the rolling or sliding of utensil 30 into inlet orifice 24. Inlet orifice 24 opens to the interior of housing 12 and may be shaped to conform to a shape of writing utensil 30. The size of inlet orifice 24 and its shape characteristics may also serve the function of preventing incompatibly shaped writing utensils and unwanted objects from being placed into housing 12. After contaminated writing utensil 30 has passed through inlet orifice 24, it is exposed to UV light inside of housing 12 as described in more detail with reference to FIGS. 3A and 3B. In FIG. 1A, door 28 is shown in a closed position wherein the outer surface of door 28 is flush with housing exterior surface 14. When in the closed position, door 28 prevents writing utensil 30 contained within housing 12 from exiting via outlet 26. It may be appreciated that a light or other similar indicator may be provided on exterior surface 14 of housing 12 to indicate when apparatus 10 is in the powered on state.

Figure 2:
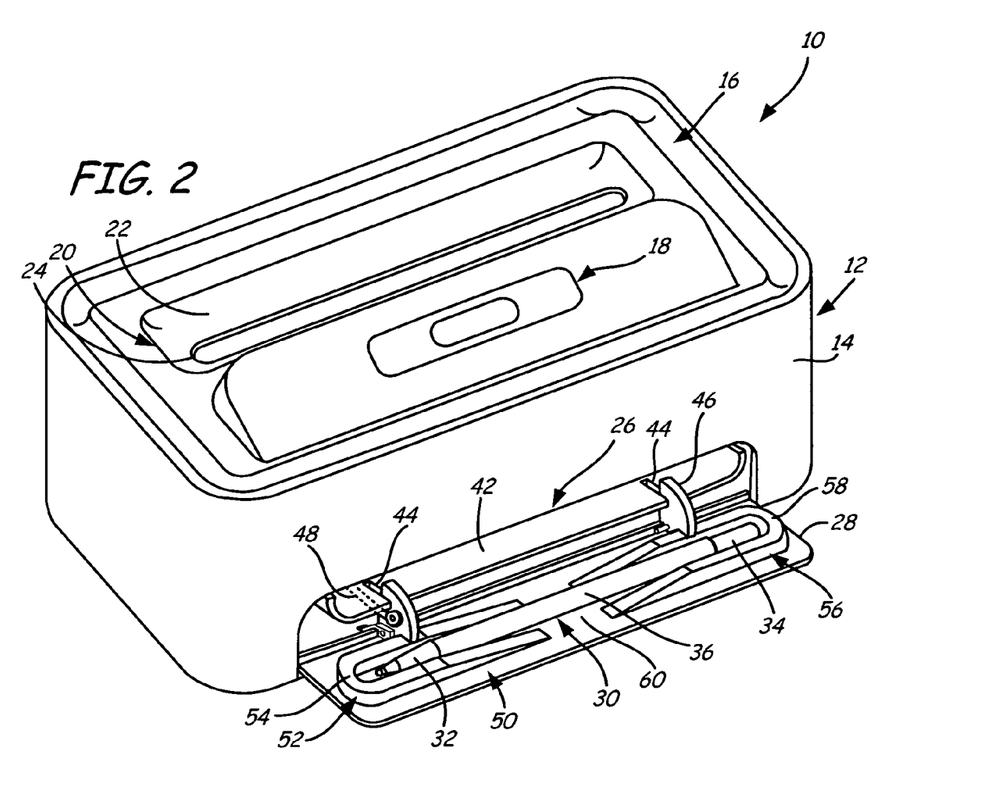
FIG. 2 is a perspective view of the front of the writing utensil sterilization apparatus with the door open.

FIG. 2 is a perspective view of the front of apparatus 10, showing ramp 42, slots 44, utensil separator 46, motor arm link 48 (in dotted lines), utensil catch 50 having first receiving element 52 including first top surface 54 and second receiving element 56 including second top surface 58, and utensil pick-up area 60. In FIG. 2, door 28 is shown in an open position, and a sterile writing utensil 30 is resting in catch 50. Details of the operation of ramp 42, slots 44, utensil separator 46, and motor arm link 48 are discussed with reference to FIGS. 3A, 4A, 4B, 5A, 5B and 5C.

To retrieve a UV-sterilized writing utensil 30 from the interior of housing 12, input is provided to user interface 18, causing door 28 to open to the position shown in FIG. 2 and allowing sterile writing utensil 30 to be retrieved from utensil catch 50. User interface 18 preferably comprises a non-contact sensing mechanism including but not limited to motion sensors, proximity sensors, optical sensors, ultrasonic sensors, and voice or audio responsive sensors. Touch-free control of door 28 to open and/or close via user interface 18 reduces the risk of disease transmission from one person to another resulting from contact with common surfaces. Nonetheless, user interface 18 may also comprise a touch-based control in combination with the touch-free control for instances where the touch-free control is non-responsive or malfunctions, for example. Examples of touch-based controls may include push buttons or membrane switches for controlling the opening and/or closing of door 28. Although user interface 18 is shown on lid 16, it may be appreciated that it can be located in other locations on apparatus 10, such as on exterior surface 14 above door 28, for example.

As shown in FIG. 2, the backside of door 28 is exposed when door 28 is in an open state, and comprises utensil catch 50 including first receiving element 52 and second receiving element 56 on either side of a pick-up area 60. Utensil catch 50 functions to hold sterilized writing utensil 30 until it is retrieved from utensil pick-up area 60. First end 32 of sterilized writing utensil 30 is held in place by first receiving element 52, and second end 34 is held in place by second receiving element 56, with each receiving element 52, 56 tapering to utensil pick-up area 60 where middle portion 36 of writing utensil 30 rests. This design allows sterilized writing utensil 30 to be picked up from utensil pick-up area 60 without having to touch any surface other than middle portion 36 of writing utensil 30. Additionally, first top surface 54 and second top surface 58 are preferably raised relative to first end 32 and second end 34 of sterilized writing utensil 30, respectively, thus providing a physical obstacle to retrieving writing utensil 30 by its first end 32 or second end 34. This design promotes the retrieval of sterilized writing utensil 30 by its middle portion 36, and thereby minimizes unwanted contact with catch 50 and/or door 28 surfaces that may cause contamination of apparatus 10 and heighten the risk of disease transmission from one user to a subsequent user. To further minimize unwanted contact with catch 50 and/or door 28 surfaces, middle portion 36 of sterilized writing utensil 30 may be suspended over pick-up area 60 by making the surface of pick-up area 60 recessed relative to a surface of first receiving element 52 and second receiving element 56 supporting first end 32 and second end 34 of writing utensil 30, respectively. This would minimize the potential for accidental contact with a backside surface of door 28 in the vicinity of pick-up area 60 when retrieving sterilized writing utensil 30 by its middle portion 36, for example.

Figure 3A:
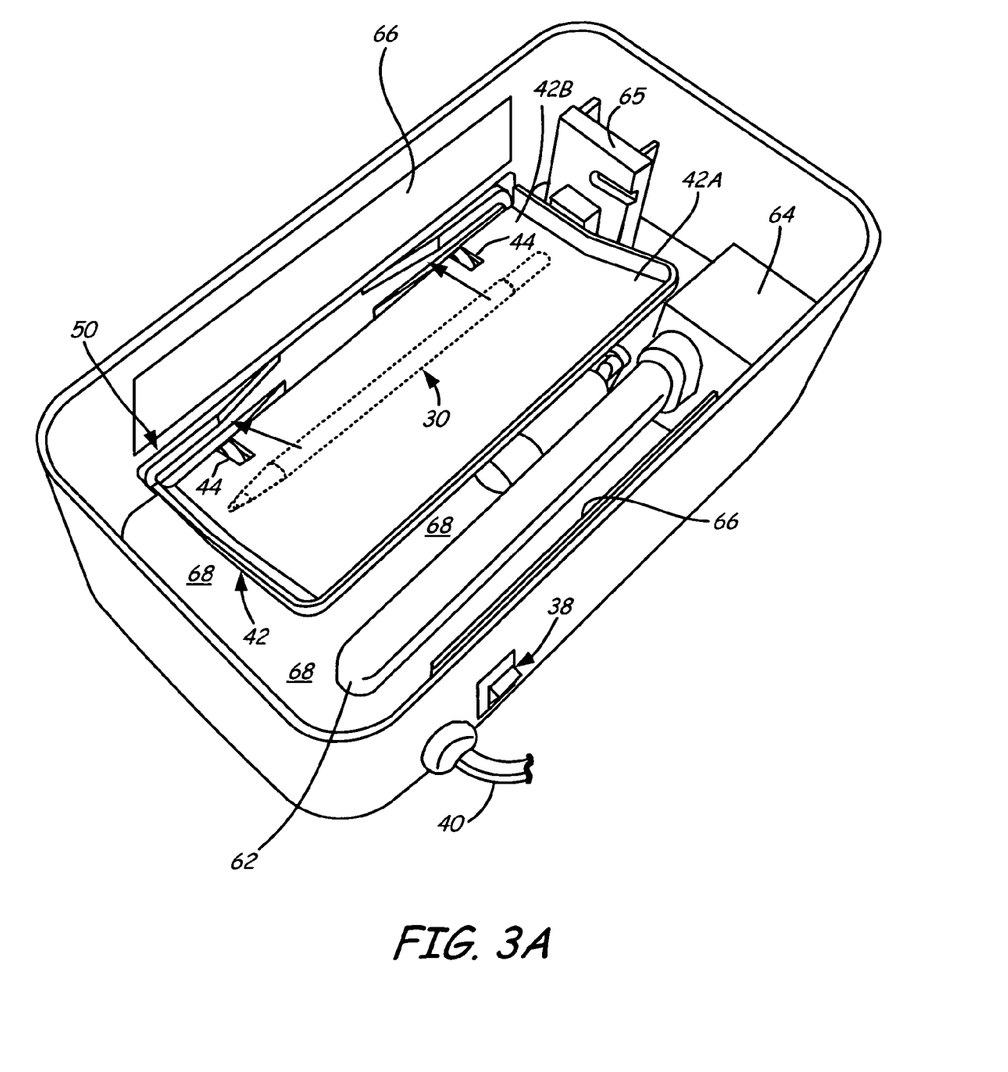
FIG. 3A is a perspective view of the rear of the writing utensil sterilization apparatus with the lid removed.
Figure 3B:
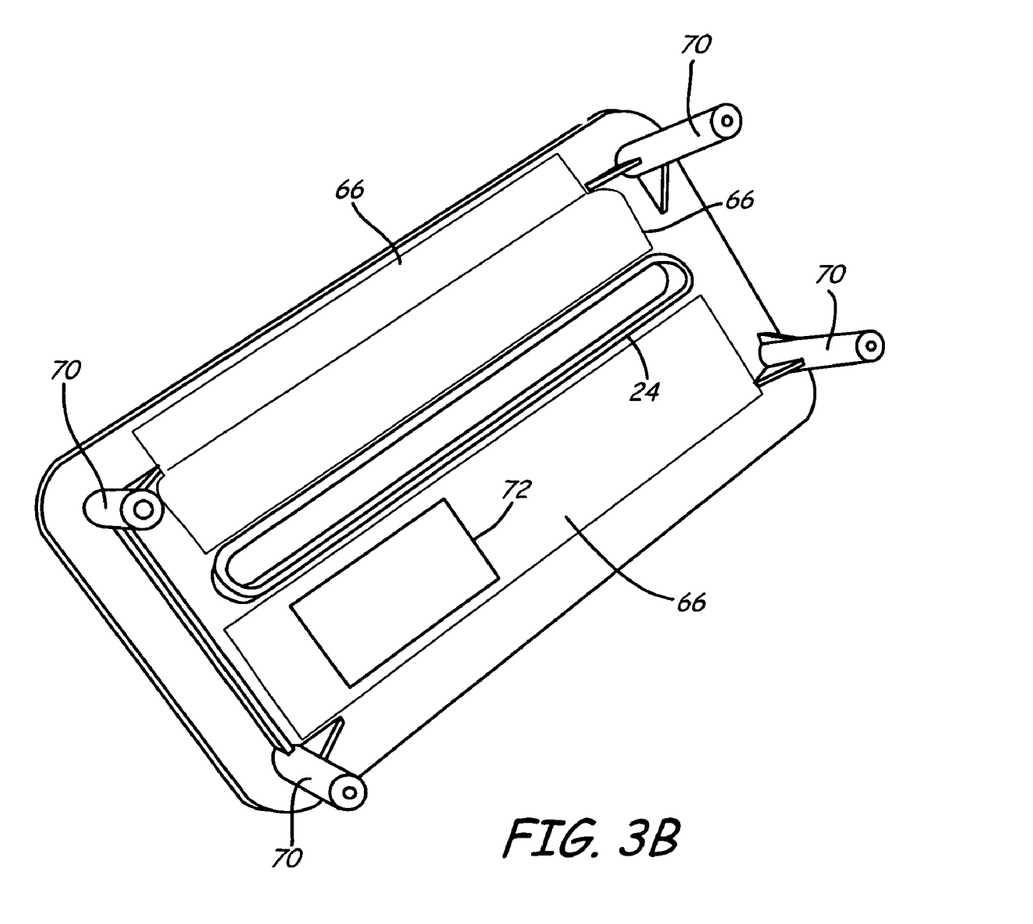
FIG. 3B is a perspective view of the lid removed from the apparatus shown in FIG. 3A.

FIG. 3A is a perspective view of the back of apparatus 10 with lid 16 removed, further showing the inside of housing 12 including UV light source 62, ballast 64, mount 65, light reflective material 66, ramp beginning 42A, ramp end 42B, and housing floor 68, wherein door 28 is in a closed position. FIG. 3B is a perspective view of the underside of lid 16 removed from the apparatus shown in FIG. 3A, showing light reflective material 66, legs 70, electrical access hole 72, and the underside of inlet orifice 24. Electrical access hole 72 allows wiring to be connected from user interface 18 to other components of apparatus 10, as described in more detail with reference to FIG. 6. Legs 70 of lid 16 allow attachment to housing floor 68 of apparatus 10.

While apparatus 10 is in the powered-on state, power is supplied to UV light source 62 such that UV light emanates in the interior space of housing 12. UV light source 62 is shown as a UV lamp requiring ballast 64, however, it may be appreciated that other UV light sources could be used, including but not limited to UV light emitting diodes. UV light source 62 should emit UV light in the germicidal wavelength of between 185-254 nanometers. If a UV lamp is used, a 6-9 watt UV lamp emitting in the germicidal wavelength spectrum is sufficient for the size of apparatus 10. Ramp 42 forms a path from inlet 20 to outlet 26 inside of housing 12 of apparatus 10. Inlet orifice 24 is positioned over ramp beginning 42A such that when a contaminated writing utensil 30 drops through inlet orifice 24, it first lands on ramp beginning 42A before proceeding to roll and/or slide in the direction of the arrows to ramp end 42B, where it is caught by catch 50 on the inside of door 28 (shown in more detail with reference to FIGS. 5A-5C). As writing utensil 30 rolls and/or slides down ramp 42, it is exposed on all sides to UV light emanating from UV light source 62 either directly or as reflected by reflective material 66, thereby disinfecting it. To assist in directing UV light onto the surfaces of writing utensil 30, light reflective material 66 is provided on the interior surfaces of housing 12, the underside surfaces of lid 16, as well as the surface of ramp 42, and may comprise mirrored Mylar, for example. Although FIG. 3A shows UV light source 62 positioned behind ramp 42, mount 65 is provided as an optional location for UV light source 62 which would position it directly above ramp 42. Writing utensil 30 should be of a generally cylindrical shape so that it may roll down ramp 42 rather than sliding all the way down on one side, for example. By rolling down ramp 42, all surfaces of writing utensil 30 may be exposed to UV light and sterilized. Examples of writing utensils having a generally cylindrical shape include pens with caps removed and pencils, although it may be appreciated that any writing utensil 30 capable of rolling on a surface may be sterilized with apparatus 10.

Figure 4A:
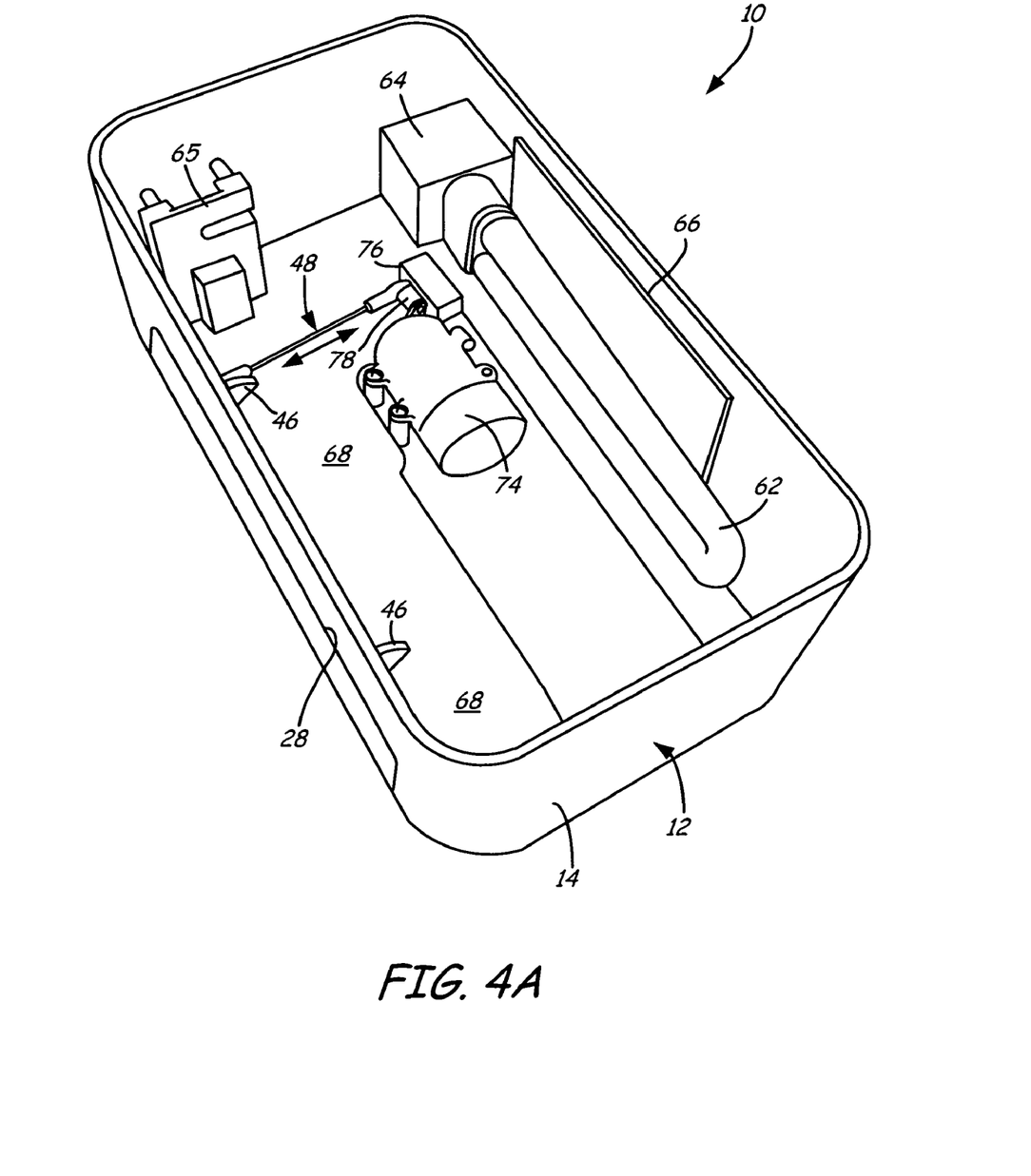
FIG. 4A is a perspective view of the front of the writing utensil sterilization apparatus with the lid and the ramp removed.
Figure 4B:
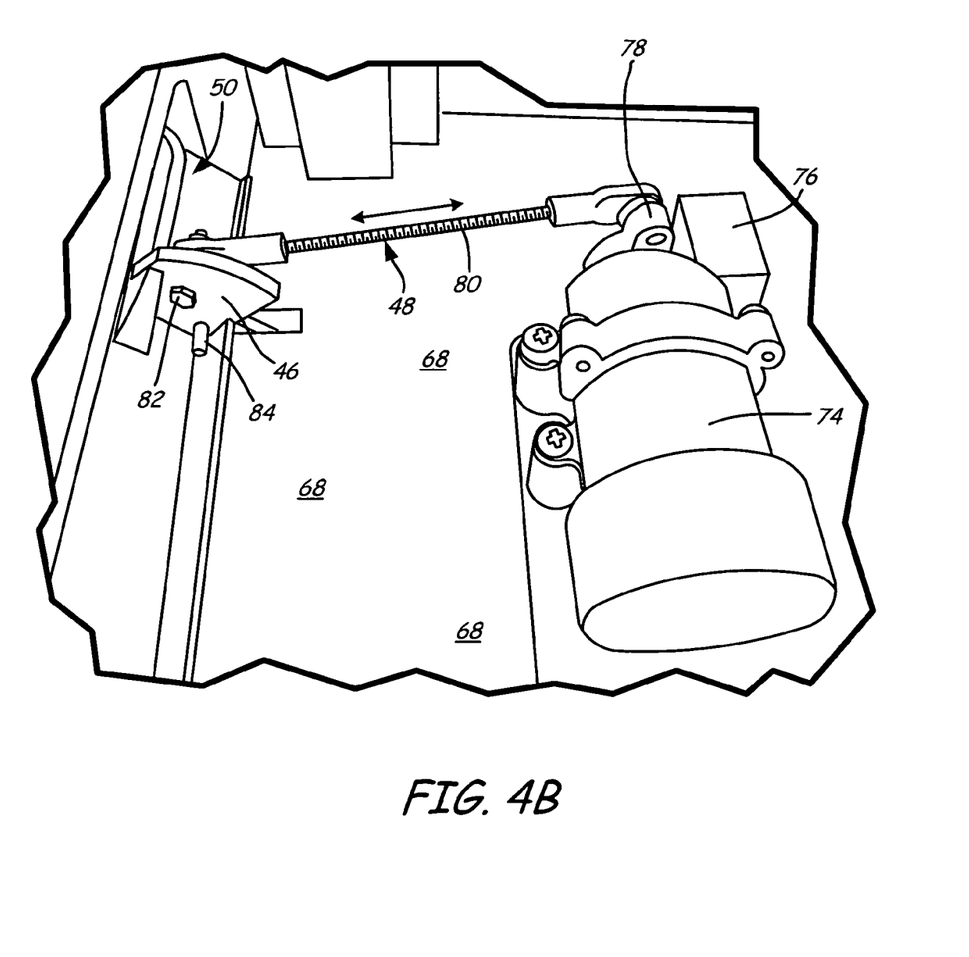
FIG. 4B is an enlarged view of FIG. 4A.

FIG. 4A is a perspective view of the front of apparatus 10 with lid 16 off and further with ramp 42 removed, showing motor arm link 48, utensil separator 46, and housing floor 68, and further showing motor 74, stop block 76, and motor arm 78. FIG. 4B is an enlarged view of FIG. 4A, further showing motor arm link 48 comprising length adjuster 80, as well as separator attachment 82 and door hinge 84.

Motor arm 78 is connected to motor arm link 48, which is in turn connected to separator 46 via separator attachment 82. Separator 46 is connected to door 28 such that movement of separator 46 causes pivoting of door 28 relative to housing 12 on door hinge 84. Motor 74 functions to move motor arm 78 in a counterclockwise and clockwise position with respect to FIGS. 4A and 4B. To prevent motor arm 78 from over-rotating, stop block 76 defines a stop position for clockwise rotation, and housing floor 68 defines a stop position for counterclockwise rotation. At resting state, motor arm 78 abuts stop block 76 to keep door 28 closed as shown in FIG. 4A. However, when an input is provided to user interface 18, motor 74 is actuated to move motor arm 78 in a counterclockwise direction until motor arm 78 abuts housing floor 68, at which point door 28 is in the open state shown in FIG. 2. As described in more detail with reference to FIGS. 5A-5C, this movement also causes rotation of utensil separator 46 into slots 44 (also shown in FIGS. 2 and 3A) to separate writing utensils resting on ramp 42. After a period sufficient to allow writing utensil 30 to be retrieved from catch 50 in door 28, motor 74 rotates motor arm 78 in a clockwise position until abutting stop block 76, thereby closing door 28 until motor 74 is once again actuated by user input. Further details of the operation of motor 74 in response to a user input are provided with reference to FIGS. 6 and 7. Although stop block 76 defines a closed state for door 28, and housing floor 68 defines an open state for door 28, length adjustor 80 is provided to fine tune the length of motor arm link 48 to compensate for motor inaccuracy and to ensure tight closing and proper opening of door 28. Length adjustor 80 may comprise a threaded link, for example.

Figure 5A:
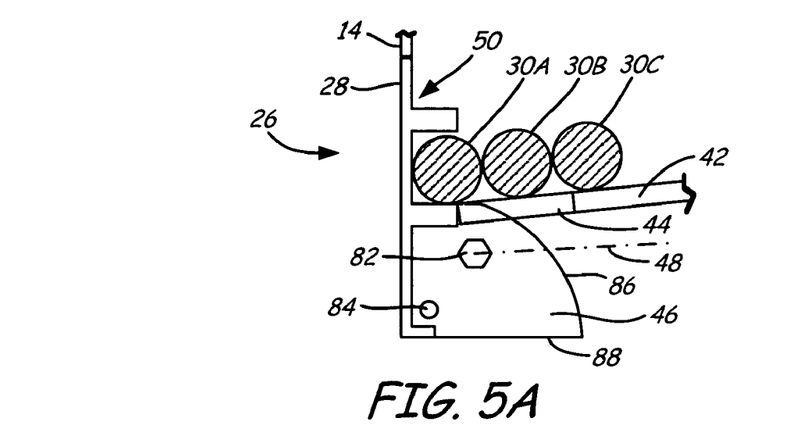
FIGS. 5A-5C are a series of sectional views of the writing utensil sterilization apparatus showing the door closed, the door partially open, and the door completely open, respectively.
Figure 5B:
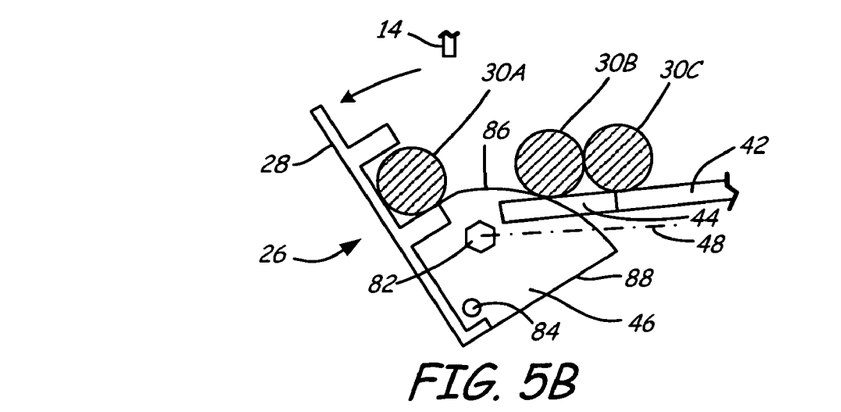
Figure 5C:
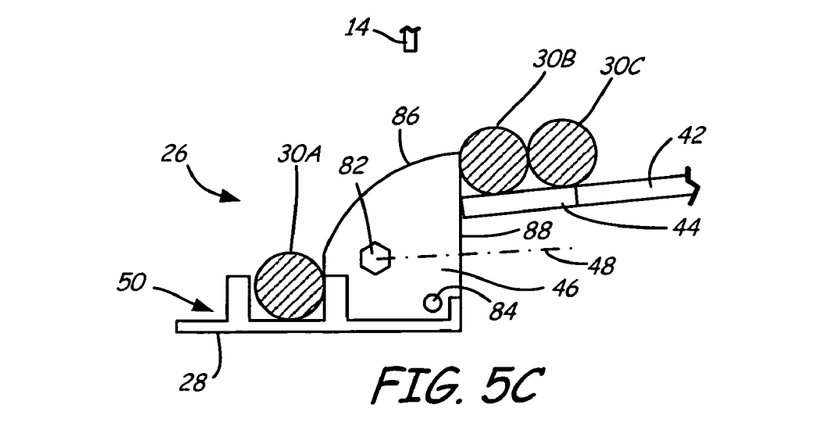

FIGS. 5A-5C are a series of sectional views of apparatus 10 illustrating the operation of utensil separator 46 further showing cam portion 86 and stop portion 88 for the separation of a single writing utensil 30A from multiple writing utensils 30A, 30B, and 30C. When multiple writing utensils 30A, 30B, and 30C have been placed in apparatus 10 and sterilized by UV light, they begin to stack up on ramp 42 in the manner shown in FIG. 5A behind writing utensil 30A held in catch 50 on the backside of door 28. As shown in FIG. 5B, as door 28 begins to open, writing utensil 30A stays in catch 50 while cam portion 86 rises through slot 44 to prevent writing utensil 30B from rolling further down ramp 42. As shown in FIG. 5C, stop portion 88 of utensil separator 46 rises through slot 44 to prevent writing utensil 30B and writing utensil 30C behind it from rolling off of ramp 42 and out of outlet 26, thereby ensuring only one writing utensil 30A is dispensed by catch 50 of door 28 each time a user input actuates the opening of door 28. Once writing utensil 30A is retrieved from catch 50, door 28 closes, stop portion 88 and cam portion 86 of utensil separator 46 move through slot 44 and out of the way of writing utensil 30B, which is then allowed to roll into catch 50. If writing utensil 30A is not retrieved from catch 50 shown in FIG. 5C, then it simply travels back to the state shown in FIG. 5A and once again abuts writing utensil 30B. Although only three writing utensils are shown in FIGS. 5A-5C, it may be appreciated that the apparatus 10 may house any number of writing utensils allowed by the total length of ramp 42, for example.

Figure 6:
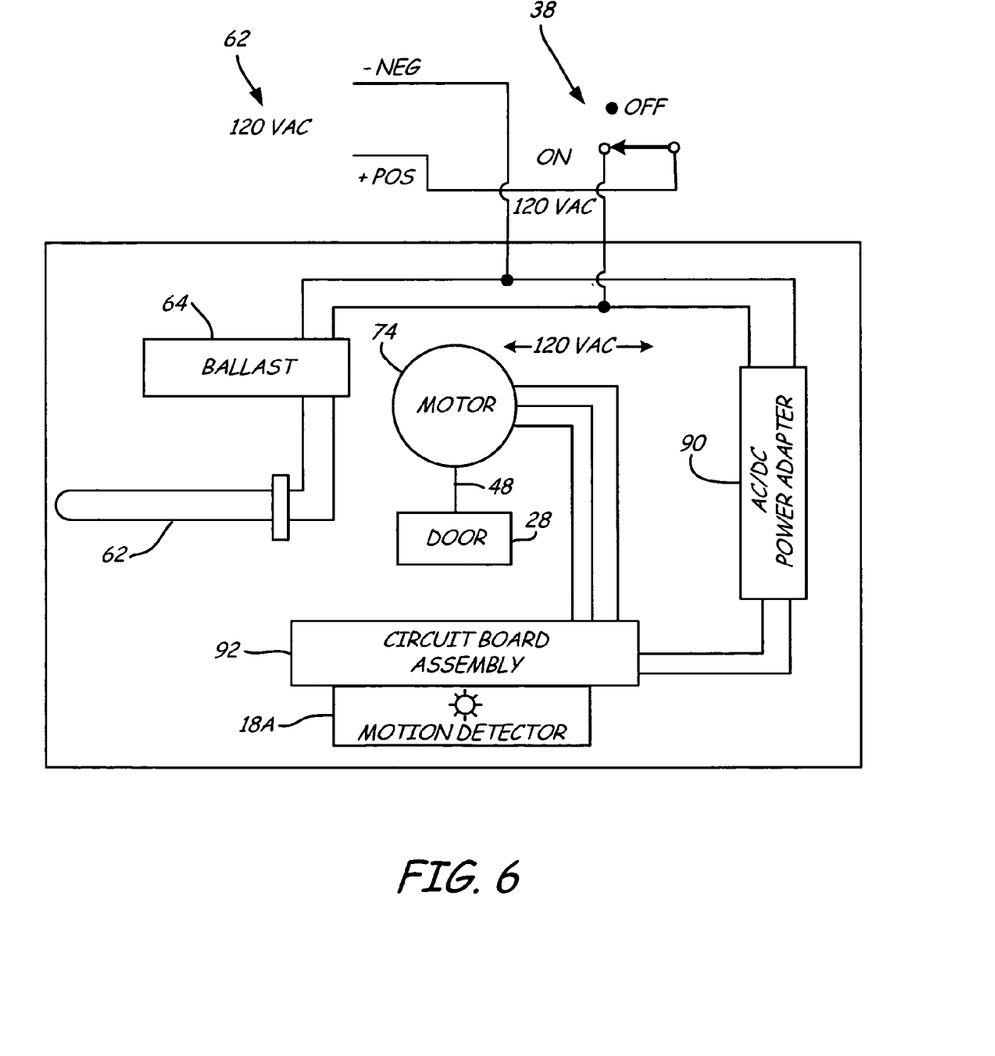
FIG. 6 is a schematic diagram of the electrical and mechanical relationships between components of the writing utensil sterilization apparatus.

FIG. 6 is a schematic diagram of electrical and mechanical relationships between components of apparatus 10, including power source 62, on/off switch 38, ballast 64, UV light source 62, motor 74, motor arm link 48, and door 28, and further showing AC/DC power adapter 90, circuit board assembly 92, and motion detector 18A used as one example of user interface 18, although other user interfaces may be used as described with reference to FIG. 2.

Power source 62 is shown as 120 VAC power in the embodiment of FIG. 6, and is supplied by power cord 40 to apparatus 10 as shown in FIG. 1B. On/off switch 38 is shown in the "on" position to allow power to flow to the components shown in FIG. 6. 120 VAC power is supplied directly to ballast 64, where current is limited to the proper value for UV light source 62, and also to AC/DC power adapter 90 to convert the alternating current to direct current for powering circuit board assembly 92, motion detector light 18A, and motor 74. AC/DC power adapter 90 and circuit board assembly 92 may be located anywhere in housing 12, for example, so long as it does not obstruct UV light from accessing ramp 42. If motion detector 18A is located in lid 16, then electrical wiring may be routed to it from AC/DC power adapter 90 through electrical access hole 72 shown in FIG. 3B, for example. Circuit board assembly 92 may be a printed circuit board containing circuitry responsive to a signal from motion detector 18A and for sending a control signal to motor 74 as a function of the signal from motion detector 18A. For example, if motion (e.g. a user input) is detected by motion detector 18A, it may send a signal to circuit board assembly 92, which in turn sends a control signal to actuate motor 74 and open door 28 via motor arm link 48.

Figure 7:
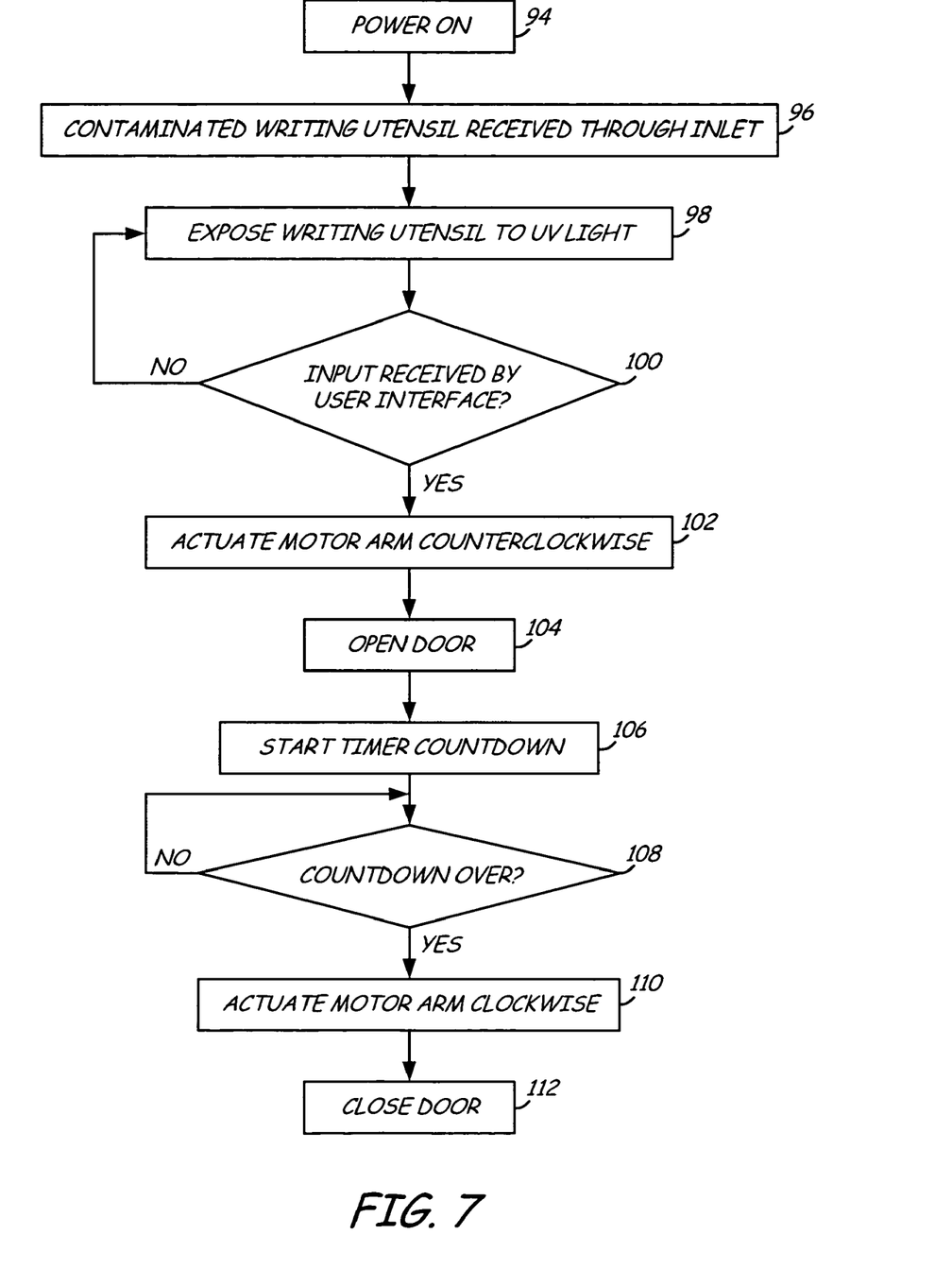
FIG. 7 is a flow diagram of the operation of the writing utensil sterilization apparatus.

FIG. 7 is a flow diagram showing the operation of apparatus 10 for sterilizing writing utensil 30. In the powered on state 94, a contaminated writing utensil 30 is received through inlet 20 of apparatus 10 (step 96). Next, the contaminated writing utensil 30 is exposed to UV light from UV light source 62 (step 98). If input has not been received by user interface 18 (step 100), writing utensil 30 continues to be exposed to UV light at step 98, whether it is held in catch 50 of door 28, or if it is stacked on ramp 42. If input has been received, then a signal is sent to motor 74 to actuate the motor arm 78 counterclockwise (step 102), thereby opening door 28 (step 104). Next, a timer countdown is initiated (step 106) to allow sufficient time for writing utensil 30 held in catch 50 of door 28 to be retrieved. A sufficient countdown time for retrieving writing utensil 30 may be between about 5-10 seconds, for example. If the countdown has not reached zero, the countdown continues (step 108). If it has reached zero, a signal is sent to motor 74 to actuate motor arm 78 clockwise (step 110), thereby closing door 28 (step 112). As described previously, door 28 may close regardless of whether writing utensil 30 has been retrieved from catch 50.

Efficacy Testing of the Apparatus for Disinfecting Contaminated Writing Utensils The following experiment was conducted to produce the results shown in TABLE 1 below. A *Staphylococcus aureus* ATCC 43300 (MRSA strain) was inoculated in duplicate onto plastic ink pens at a titer of $6 \times 10^6$. The organisms were allowed to dry 16-24 hours at ambient conditions. After drying, the pens were individually placed into apparatus 10 as follows: Two pens (A1 and B1) were exposed to UV light in apparatus 10 for 10 seconds, two pens (A2 and B2) were exposed for 30 seconds, two pens (A3 and B3) were exposed for 1 minute, and two pens (A4 and B4) were exposed for 5 minutes. There were three inoculated control test pens (CP1, CP2, and CP3) and three negative control test pens (CN1, CN2, and CN3). Each of the pens was sampled with a cotton-tipped swab moistened with Dey-Engley broth. After sampling, the swab was transferred to a tube containing 1 mL of Butterfield's phosphate dilution buffer, vortexed for 1 minute and then serially diluted and plated onto Baird-Parker agar. The plates were incubated at 35° C. for 48 hours and then the colonies were counted. A 3 log reduction in organism titer is considered 99.9% germ free.

TABLE 1 shows the results of the efficacy testing of apparatus 10, including the number of colonies for each serial dilution, including those too numerous to count ("TNTC"), as well as estimated colony forming units ("CFU") per milliliter of dilution buffer.

TABLE 1

| Exposure Time | Duplicates | Dilution | | | CFU/mL | Average Reduction |
| --- | --- | --- | --- | --- | --- | --- |
| | | Direct | −1 | −2 | | |
| 10 sec | A1 | 19 | 2 | | 950 est. | 65% |
| | B1 | 0 | | | <1 est. | |
| 30 sec | A2 | 7 | 0 | | 350 est. | 99.4% |
| | B2 | 2 | 0 | | 100 est. | |

TABLE 1-continued

| Exposure Time | Duplicates | Dilution | | | CFU/mL | Average Reduction |
| --- | --- | --- | --- | --- | --- | --- |
| | | Direct | −1 | −2 | | |
| 1 min | A3 | 0 | | | <1 est. | 100% |
| | B3 | 0 | | | <1 est. | |
| 5 min | A4 | 0 | | | <1 est. | 100% |
| | B4 | 0 | | | <1 est. | |
| Pos. Control | CP1 | TNTC | 27 | 3 | 13,500 | |
| | CP2 | TNTC | TNTC | 14 | 70,000 | |
| | CP3 | TNTC | 42 | 0 | 21,000 | |
| | | | | Average per Positive Control | 34,833 | |
| Neg. Control | CN1 | 0 | | | <1 est. | |
| | CN2 | 0 | | | <1 est. | |
| | CN3 | 0 | | | <1 est. | |

As shown in Table 1, exposure to UV light in apparatus 10 for 10 seconds reduced the inoculum by and average of 65%. At 30 seconds of exposure the inoculum was reduced by an average of 99.4%. At both 1 minute and 5 minutes of exposure no organisms were recovered, which is a 100% reduction.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A writing utensil sterilization apparatus comprising:
   a housing comprising an inlet for receiving a writing utensil into the housing and an outlet for dispensing the writing utensil from the housing;
   a UV light source disposed within the housing for emitting UV light; and
   a path disposed within the housing for guiding the writing utensil from the inlet to the outlet while exposing the writing utensil to the UV light.

2. The writing utensil sterilization apparatus of claim 1, wherein the inlet comprises a sloping surface for guiding the writing utensil to the path disposed within the housing.

3. The writing utensil sterilization apparatus of claim 1, wherein the inlet comprises an orifice having the shape of a slot.

4. The writing utensil sterilization apparatus of claim 1, wherein the housing comprises a lid, and wherein the inlet is disposed in the lid of the housing.

5. The writing utensil sterilization apparatus of claim 1, wherein the outlet comprises a door having a front side and a back side.

6. The writing utensil sterilization apparatus of claim 5, further comprising a motor disposed within the housing, and wherein the door is connected to the motor.

7. The writing utensil sterilization apparatus of claim 6, further comprising a user interface for actuating the motor as a function of a user input to open the door.

8. The writing utensil sterilization apparatus of claim 7, wherein the user interface is a touch-free interface.

9. The writing utensil sterilization apparatus of claim 8, wherein the touch-free interface is selected from a group consisting of motion sensors, proximity sensors, optical sensors, ultrasonic sensors, and voice or audio responsive sensors.

10. The writing utensil sterilization apparatus of claim 9, wherein the user interface further comprises a touch-based interface in addition to the touch-free interface.

11. The writing utensil sterilization apparatus of claim 8, wherein the door comprises a catch disposed on the back side of the door for receiving the writing utensil.

12. The writing utensil sterilization apparatus of claim 11, wherein the catch comprises a first receiving element in contact with a first end of the writing utensil and a second receiving element in contact with a second end of the writing utensil.

13. The writing utensil sterilization apparatus of claim 12, wherein a utensil pick-up area is located between the first receiving element and the second receiving element over which a middle portion of the writing utensil is suspended.

14. The writing utensil sterilization apparatus of claim 1, wherein a surface disposed within the housing comprises reflective material for directing the UV light to contact the writing utensil as it is guided by the path.

15. The writing utensil sterilization apparatus of claim 14, wherein the surface comprises a surface of the path.

16. The writing utensil sterilization apparatus of claim 15, wherein the path comprises a ramp extending between the inlet and the outlet.

17. The writing utensil sterilization apparatus of claim 1, further comprising a utensil separator for separating one writing utensil from a plurality of writing utensils disposed on the path.

18. The writing utensil sterilization apparatus of claim 1, wherein the outlet is disposed in a front portion of the housing.

19. A writing utensil sterilization apparatus comprising:
   a user interface for receiving a user input;
   an enclosure having an inlet for receiving a writing utensil into the enclosure and an outlet for dispensing the writing utensil from the enclosure in response to the user input;
   a UV light source disposed within the enclosure for emitting UV light enclosed by the enclosure; and
   a ramp disposed within the enclosure extending between the inlet and the outlet for guiding the writing utensil from the inlet to the outlet in exposure to the UV light.

20. The writing utensil sterilization apparatus of claim 19, wherein the user interface includes a touch-free sensor.

* * * * *